United States Patent
Skilling

(10) Patent No.: US 6,489,121 B1
(45) Date of Patent: Dec. 3, 2002

(54) METHODS OF IDENTIFYING PEPTIDES AND PROTEINS BY MASS SPECTROMETRY

(75) Inventor: John Skilling, Kenmare (IE)

(73) Assignee: Micromass Limited, Manchester (GB)

( * ) Notice: Subject to any disclaimer, the term of this patent is extended or adjusted under 35 U.S.C. 154(b) by 0 days.

(21) Appl. No.: 09/544,146

(22) Filed: Apr. 6, 2000

(30) Foreign Application Priority Data

Apr. 6, 1999 (GB) .............................................. 9907810
Apr. 16, 1999 (GB) .............................................. 9908684

(51) Int. Cl.$^7$ ........................ G01N 33/53; G01N 31/00; B01D 59/44; H01J 49/00
(52) U.S. Cl. ........................ 435/7.1; 250/281; 250/282; 250/287; 364/489; 702/22
(58) Field of Search .......................... 435/7.1; 250/281, 250/282, 287; 364/489; 702/22

(56) References Cited

U.S. PATENT DOCUMENTS

| | | | |
|---|---|---|---|
| 3,982,101 A | * | 9/1976 | Kalb et al. .................. 235/152 |
| 5,731,983 A | * | 3/1998 | Balakrishnan et al. ...... 364/489 |
| 6,004,267 A | | 12/1999 | Tewari ........................ 600/300 |
| 6,029,114 A | * | 2/2000 | Shamovsky et al. .......... 702/22 |

FOREIGN PATENT DOCUMENTS

| | | |
|---|---|---|
| GB | WO 95/25281 | 9/1995 |
| GB | 2325465 | 11/1998 |

OTHER PUBLICATIONS

Yates, III, J. of Mass Spectrom., 1998, vol. 33, pp. 1–19.
Papayannopoulos, Mass Spectrom. Rev., 1995., vol. 14, pp. 49–73.
Yates, III, McCormack and Eng, Anal. Chem., 1996, vol. 68(17), pp. 534A–540A.
Hunt, Yates III, et al., Proc. Nat. Acad. Sci. USA, 1986, vol. 83, pp. 6233–6237.
Sakurai, Matsuo, Matsuda and Katakuse, Biomed. Mass Spectrom., 1984, vol. 11 (8), pp. 397–399.
Hamm, Wilson and Harvan, CABIOS, 1986, vol. 2 (2), pp. 115–118.
Ishikawa and Niwa, Biomed. and Environ. Mass Spectrom., 1986, vol. 13, pp. 373–380.
Yates III, Speicher et al., Analytical Biochemistry, 1993, vol. 214, pp. 397–408.
Yates III, Eng et al., Anal. Chem., 1995, vol. 67, pp. 1426–1436.
Figeys et al., Rapid Comm. in Mass Spectrom., 1998, vol. 12, pp. 1435–1444.
Mortz et al., Proc. Nat. Acad. Sci. USA, 1996, vol. 93, pp. 8264–8267.
Jaffe et al., Biochemistry, 1998, vol. 37, pp. 16211–16224.
Arnott et al., Electrophoresis, 1998, vol. 19, pp. 968–980.
Shevchenko et al., J. Protein Chem., 1997, vol. 16 (5), pp. 481–490.
Eng et al., J. Am. Soc. Mass Spectrom., 1994, vol. 5, pp. 976–989.
Pappin, Hojrup and Bleasby, Current Biology, 1993, vol. 3 (6), pp. 327–332.
Yates, III, Eng and McCormack, Anal. Chem., 1995, vol. 67 (18), pp. 3202–3210.
Dongre, Eng and Yates III, Trends in Biotechnology, 1997, vol. 15. pp. 418–425.
Yates III, Electrophoresis, 1998, vol. 19, pp. 893–900.
Shevchenko, Wilm, Vorm et al., Techniques group, British Mass Spectrom. Soc. Joint colloquium, 1996, pp. 893–897.
Delgoda and Pulfer, J. Chem. Inf. Computer Sci., 1993, vol. 33, pp. 332–337.

* cited by examiner

*Primary Examiner*—W. Gary Jones
*Assistant Examiner*—Arun K. Chakrabarti
(74) *Attorney, Agent, or Firm*—Diederiks & Whitelaw, PLC

(57) ABSTRACT

A method of identifying a protein, polypeptide or peptide by means of mass spectrometry and especially by tandem mass spectrometry is disclosed. The method preferably models the fragmentation of a peptide or protein in a tandem mass spectrometer to facilitate comparison with an experimentally determined spectrum. A fragmentation model is used which takes account of all possible fragmentation pathways which a particular sequence of amino acids may undergo. A peptide or protein may be identified by comparing an experimentally determined mass spectrum with spectra predicted using such a fragmentation model from a library of known peptides or proteins. Alternatively, a de novo method of determining the amino acid sequence of an unknown peptide using such a fragmentation model may be used.

29 Claims, 2 Drawing Sheets

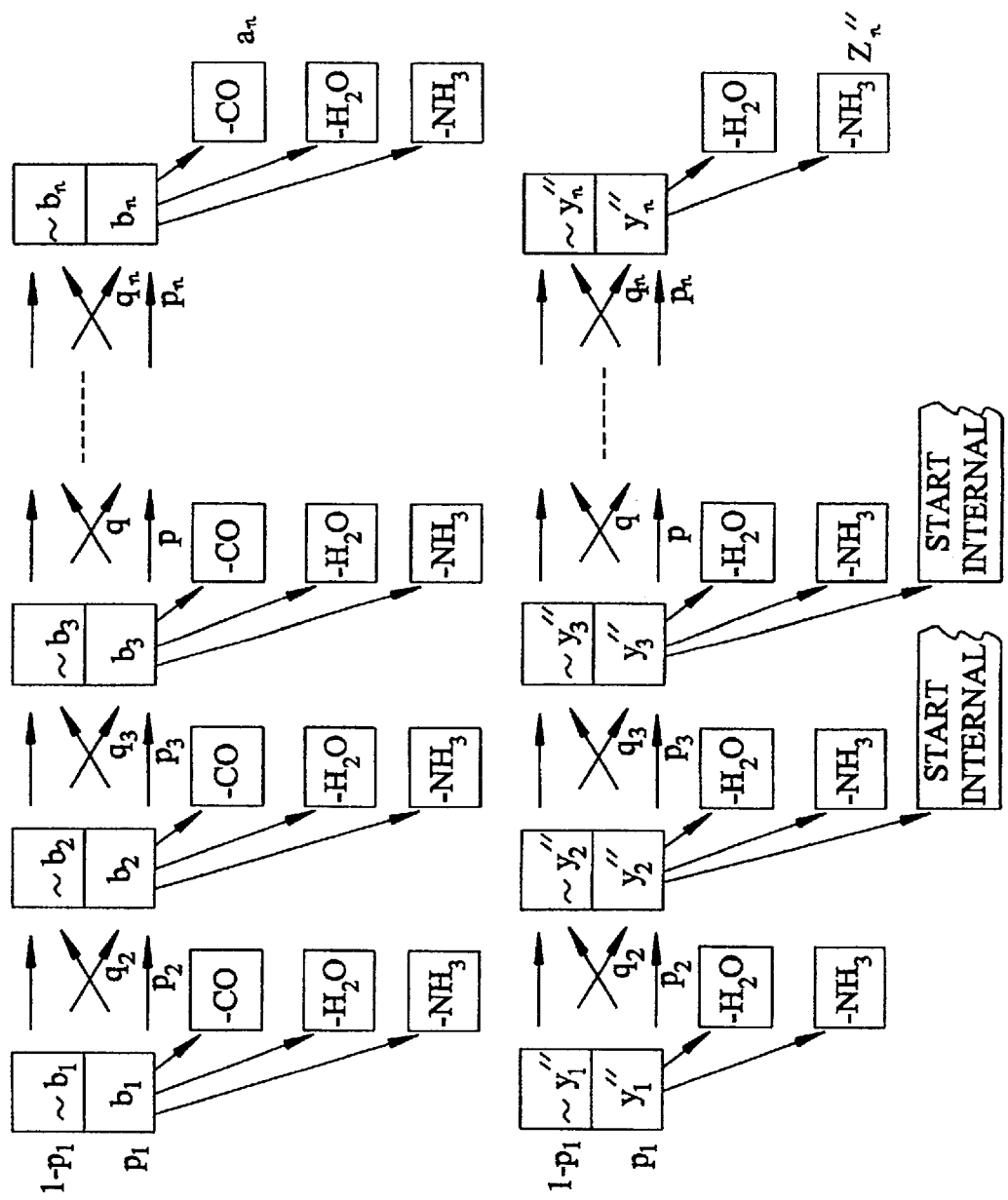

METHODS OF IDENTIFYING PEPTIDES AND PROTEINS BY MASS SPECTROMETRY

BACKGROUND OF THE INVENTION

1. Field of the Invention

This invention relates to methods of identifying a protein, polypeptide or peptide by means of mass spectrometry and especially by tandem mass spectrometry (MS/MS). Preferred methods relate to the use of mass spectral data to identify an unknown protein where sequence is at least partially present in an existing database.

2. Discussion of the Prior Art

Although several well-established chemical methods for the sequencing of peptides, polypeptides and proteins are known (for example, the Edman degradation), mass spectrometric methods are becoming increasingly important in view of their speed and ease of use. Mass spectrometric methods have been developed to the point at which they are capable of sequencing peptides in a mixture without any prior chemical purification or separation, typically using electrospray ionization and tandem mass spectrometry (MS/MS). For example, see Yates III (J. Mass Spectrom, 1998 vol. 33 pp. 1–19), Papayannopoulos (Mass Spectrom. Rev. 1995, vol. 14 pp. 49–73), and Yates III, McCormack, and Eng (Anal. Chem. 1996 vol. 68 (17) pp. 534A–540A). Thus, in a typical MS/MS sequencing experiment, molecular ions of a particular peptide are selected by the first mass analyzer and fragmented by collisions with neutral gas molecules in a collision cell. The second mass analyzer is then used to record the fragment ion spectrum that generally contains enough information to allow at least a partial, and often the complete, sequence to be determined.

Unfortunately, however, the interpretation of the fragment spectra is not straightforward. Manual interpretation (see, for example, Hunt, Yates III, et al, Proc. Nat. Acad. Sci. USA, 1986, vol. 83 pp 6233–6237 and Papayannopoulos, ibid) requires considerable experience and is time consuming. Consequently, many workers have developed algorithms and computer programs to automate the process, at least in part. The nature of the problem, however, is such that none of those so far developed are able to provide in reasonable time complete sequence information without either requiring some prior knowledge of the chemical structure of the peptide or merely identifying likely candidate sequences in existing protein structure databases. The reason for this will be understood from the following discussion of the nature of the fragment spectra produced.

Typically, the fragment spectrum of a peptide comprises peaks belonging to about half a dozen different ion series each of which correspond to different modes of fragmentation of the peptide parent ion. Each typically (but not invariably) comprises peaks representing the loss of successive amino acid residues from the original peptide ion. Because all but two of the 20 amino acids from which most naturally occurring proteins are comprised have different masses, it is therefore possible to establish the sequence of amino acids from the difference in mass of peaks in any given series which correspond to the successive loss of an amino acid residue from the original peptide. However, difficulties arise in identifying to which series an ion belongs and from a variety of ambiguities that can arise in assigning the peaks, particularly when certain peaks are either missing or unrecognized. Moreover, other peaks are typically present in a spectrum due to various more complicated fragmentation or rearrangement routes, so that direct assignment of ions is fraught with difficulty. Further, electrospray ionization tends to produce multiply charged ions that appear at correspondingly rescaled masses, which further complicates the interpretation of the spectra. Isotopic clusters also lead to proliferation of peaks in the observed spectra. Thus, the direct transformation of a mass spectrum to a sequence is only possible in trivially small peptides.

The reverse route, transforming trial sequences to predicted spectra for comparison with the observed spectrum, should be easier, but has not been fully developed. The number of possible sequences for any peptide ($20^n$, where n is the number of amino acids comprised in the peptide) is very large, so the difficulty of finding the correct sequence for, say, a peptide of a mere 10 amino acids ($20^{10}=10^{13}$ possible sequences) will be appreciated. The number of potential sequences increases very rapidly both with the size of the peptide and with the number (at least 20) of the residues being considered.

Details of the first computer programs for predicting probable amino acid sequences from mass spectral data appeared in 1984 (Sakurai, Matsuo, Matsuda, Katakuse, Biomed. Mass Spectrom, 1984, vol. 11 (8) pp 397–399). This program (PAAS3) searched through all the amino acid sequences whose molecular weights coincided with that of the peptide being examined and identified the most probable sequences with the experimentally observed spectra. Hamm, Wilson and Harvan (CABIOS, 1986 vol. 2 (2) pp 115–118) also developed a similar program.

However, as pointed out by Ishikawa and Niwa (Biomed. and Environ. Mass Spectrom. 1986, vol. 13 pp 373–380), this approach is limited to peptides not exceeding 800 daltons in view of the computer time required to carry out the search. Parekh et al in UK patent application 2,325,465 (published November 1998) have resurrected this idea and give an example of the sequencing of a peptide of 1000 daltons which required $2 \times 10^6$ possible sequences to be searched, but do not specify the computer time required. Nevertheless, despite the increase in the processing speed of computers between 1984 and 1999, a simple search of all possible sequences for a peptide of molecular weights greater than 1200 daltons is still impractical in a reasonable time using the personal computer typically supplied for data processing with most commercial mass spectrometers.

This problem has long been recognized and several approaches to rendering the problem more tractable have been described. One of the most successful has been to correlate the mass spectral data with the known amino acid sequences comprised in a protein database rather than with every possible sequence. In the prior method known as peptide mass mapping, a protein may be identified by merely determining the molecular weights of the peptides produced by digesting it with a site-specific protease and comparing the molecular weights with those predicted from known proteins in a database. (See, for example, Yates, Speicher, et al in Analytical Biochemistry, 1993 vol 214 pp 397–408). However, mass mapping is ineffective if a protein or peptide comprises only a small number of amino acids residues or possible fragments, and is inapplicable if information about the actual amino acid sequences is required. As explained, tandem mass spectrometry (MS/MS) can be used to provide such sequence information. MS/MS spectra usually contain enough detail to allow a peptide to be at least partially, and often completely sequenced without reference to any database of known sequences (See copending application GB 9907810.7, filed Apr. 6, 1999). There are, however, many circumstances where it is adequate, or even preferred, to establish sequences by reference to an existing database.

Such methods were pioneered by Yates, et al, see, for example, PCT application 95/25281, Yates (J. Mass Spectrom 1998 vol 33 pp 1–19), Yates, Eng et al (Anal. Chem. 1995 vol 67 pp 1426–33). Other workers, including Mortz et al (Proc. Nat. Acad. Sci. USA, 1996 vol 93 pp 8264–7), Figeys, et al (Rapid Commun. Mass Spectrom. 1998 vol 12 pp 1435–44), Jaffe, et al, (Biochemistry, 1998 vol 37 pp 16211–24), Amot et al (Electrophoresis, 1998 vol 19 pp 968–980) and Shevchenko et al (J. Protein Chem. 1997 vol 16 (5) pp 481–490) report similar approaches.

As explained, it is generally easier to predict a fragmentation mass spectrum from a given amino acid sequence than to carry out the reverse procedure when comparing experimental MS data with sequence databases. A "fragmentation model" that describes the various ways in which a given amino acid sequence may fragment is therefore required. The chemical processes which result in fragmentation are fairly well understood, but because the number of possible routes increases very rapidly with the number of amino acid residues in a sequence it is difficult to build this knowledge into a definite model. The fragmentation models so far proposed (for example Eng et al, J. Am. Soc. Mass Spectrom, 1994 vol 5 pp 976–89) typically incorporate only a small number of possible fragmentation routes and typically produce a predicted spectrum in which all the mass peaks have equal probability. This constrained approach compromises the accuracy of the comparison with an experimental spectrum, which is likely to represent the sum of many different fragmentation pathways operating simultaneously with different degrees of importance. Consequently the degree of confidence that can be placed in the identification of a sequence on the basis of the prior fragmentation models is reduced and the chance of an incorrect identification is increased.

As explained in our copending application (GB 9907810.7, filed Apr. 6, 1999) a realistic fragmentation model is also required to predict spectra from pseudo-randomly generated trial sequences (as opposed to existing sequences comprised in a database). The fragmentation models described in the present application are applicable to both approaches.

SUMMARY OF THE INVENTION

It is an object of the present invention to provide an improved method of modelling the fragmentation of a peptide or protein in a tandem mass spectrometer to facilitate comparison with an experimentally determined spectrum. It is another object of the invention to provide such a fragmentation model which takes account of all possible fragmentation pathways which a particular sequence of amino acids may undergo. A further object of the invention is to provide methods of identifying a peptide or protein by comparing an experimentally determined mass spectrum with spectra predicted using such a fragmentation model from a library of known peptides or proteins. It is yet another object of the invention to provide a de novo method of determining the amino acid sequence of an unknown peptide using such a fragmentation model.

In accordance with these objectives the invention provides a method of identifying the most probable amino acid sequences which would account for the mass spectrum of a protein or peptide, said method comprising the steps of:
  a) producing a processable mass spectrum from said peptide; and
  b) using a fragmentation model to calculate the likelihood that any given trial amino acid sequence would account for said processable spectrum, said fragmentation model comprising the step of summing probabilistically a plurality of fragmentation routes which together represent the possible ways that said trial sequence might fragment in accordance with a set of predefined rules, each said fragmentation route being assigned a prior probability appropriate to the chemical processes involved.

In preferred methods, said plurality of fragmentation routes represent all the possible ways that a said trial sequence might fragment.

Preferably the fragmentation model is based on the production of at least two series of ions, the b series (which comprises ions representing the N-terminal residue of the trial sequence and the loss of C-terminal amino acid residues), and the y" series (which comprises ions representing the C-terminal residue and the loss of N-terminal amino acid residues). Each family of ions behaves as a coherent series, with neighbouring ions likely to be either both present or both absent. This behaviour may be described by a Markov chain, in which the probability of an ion being observed is influenced by whether or not its predecessor was observed. The parameters of the chain may be adjusted to take account of the proton affinities of the residues and their physical bond strengths. The fragmentation model may be refined by including other ion series, particularly the a series (b ions which have lost CO), the z" series (y" ions which have lost $NH_3$), and the more general loss of $NH_3$ or $H_2O$, again taking account of the probability of the chemical processes involved. Immonium ions equivalent to the loss of CO and H from the various amino acid residues may also be included. Further, the fragmentation model may comprise the generation of sub-sequences of amino acids, that is, sequences that begin and end at amino acid residues internal to the unknown peptide. It will be appreciated that the more realistic is the fragmentation model, the better will be the accuracy and fidelity of the computation of the most probable sequences. It is therefore envisaged that different fragmentation models may be employed if advances are made in understanding the chemical mechanism by which the mass spectrum of the peptide is produced.

Each of the chemical processes described above may be assigned a prior probability on the basis of the physical strength of the bonds broken in the proposed fragmentation step and the proton affinities of the various amino acid residues, thereby enabling the prior probability of each complete fragmentation route to be calculated. However, using Markov chains to model each of the ion series produced (eg, the b or y" series) means that it is unnecessary to compute an explicit spectrum for every possible fragmentation route for comparison with the processable spectrum. Instead, the method of the invention arrives at the same result by using the Markov chain representation of the various ion series to factorize the comparison, so that the likelihood summed over all the fragmentation routes can be computed in polynomial time (in the most preferred embodiment, linear time). This summed likelihood is a better basis for comparison with the processable spectrum than the likelihood or other score derived from a single fragmentation route, such as would be produced by prior fragmentation models, because the fragmentation of a real peptide involves many simultaneous routes. By the use of a fully probabilistic fragmentation model, therefore, the method of the invention automatically accounts in a quantitative sense, for this multiplicity of routes.

As explained, using Markov chains to model the fragmentation process allows the sum over all the possible fragmentation patterns to be calculated in linear time (ie, in a time proportional to the number of amino acid residues in the peptide) rather than in a time proportional to the exponentially large number of fragmentation patterns themselves. However, it will be appreciated that the invention is not limited to the particular fragmentation model described above, but includes any probabilistic fragmentation model that can be integrated computationally in polynomial time.

It will be appreciated that trial sequences used in the method of the invention may be obtained from one or more libraries or databases containing sequences or partial sequences of known peptides and proteins, or may be generated pseudo-randomly in a de-novo sequencing method, as described in our co-pending patent application (GB 9907810.7, filed Apr. 6, 1999). For example, a fragmentation model according to the invention may be used to calculate the likelihood of amino acid sequences comprised in an existing protein or peptide database accounting for an experimentally observed mass spectrum of a peptide. In this way the peptide, and/or the protein from which it is derived, may be identified. Conveniently, in such a method, only sequences or partial sequences having a molecular weight in a given range are selected from the database for input to the fragmentation model.

The method of the invention assigns a likelihood factor to each trial amino acid sequence considered. The most probable amino acid sequences in the database (or pseudo-randomly generated sequences) which would account for the processable spectrum may then be identified as the trial sequences with the highest likelihood factors. However, a more precise method that is particularly appropriate in the case of de novo sequencing, is to use a Bayesian approach. Each trial sequence is assigned a prior probability on the basis of whatever information is known about it, including its relationship to the sample from which the processable spectrum is obtained. For example, in true de novo sequencing the prior probability of a trial sequence may be based on the average natural abundances of the amino acid residues it comprises. In the case of database searches, it may be known, for example, that the sample is derived from a yeast protein, in which case, sequences in the database derived from yeasts may be assigned a higher prior probability.

The probability of a trial sequence accounting for the processable spectrum is then calculated by Bayes' theorem, that is:

Probability (trial sequence AND processable spectrum)=Prior probability (trial sequence)×likelihood factor In Bayesian terminology, the likelihood factor is:

Probability (processable spectrum GIVEN trial sequence).

Although in certain simple cases the processable mass spectrum may simply be the observed mass spectrum, it is generally preferable to convert the observed spectrum into a more suitable form before attempting to sequence the peptide. Preferably, the processable spectrum is obtained by converting multiply-charged ions and isotopic clusters of ions to a single intensity value at the mass-to-charge ratio corresponding to a singly-charged ion of the lowest mass isotope, and calculating an uncertainty value for the actual mass and the probability that a peak at that mass-to-charge ratio has actually been observed. Conveniently, the uncertainty value of a peak may be based on the standard deviation of a Gaussian peak representing the processed peak and the probability that a peak is actually observed may be related to the signal-to-noise ratio of the pea k in the observed spectrum. The program "MaxEnt3™" available from Micromass UK Ltd. may be used to produce the processable spectrum from an observed spectrum.

In order to carry out the methods of the invention a sample comprising one or more unknown peptides may be introduced into a tandem mass spectrometer and ionized using electrospray ionization. The molecular weights of the unknown peptides may typically be determined by observing the molecular ion groups of peaks in a mass spectrum of the sample. The first analyzer of the tandem mass spectrometer may then be set to transmit the molecular ion group of peaks corresponding to one of the unknown peptides to a collision cell, in which the molecular ions are fragmented by collision with neutral gas molecules. The second mass analyzer of the tandem mass spectrometer may then be used to record an observed fragmentation mass spectrum of the peptide. A processable mass spectrum may then be derived from the observed spectrum using suitable computer software, as explained. If the sample comprises a mixture of peptides, for example as might be produced by a tryptic digest of a protein, further peptides may be analyzed by selecting the appropriate molecular ion group using the first mass analyzer.

Viewed from another aspect the invention provides apparatus for identifying the most likely sequences of amino acids in an unknown peptide, said apparatus comprising a mass spectrometer for generating a mass spectrum of a said unknown peptide and data processing means programmed to:

a) Process data generated by said mass spectrometer to produce a processable mass spectrum; and b) Calculate the likelihood that any given trial amino-acid sequence would account for said processable spectrum using a fragmentation model which sums probabilistically over a plurality of fragmentation routes which together represent the possible ways that said trial sequence might fragment in accordance with a set of predefined rules, each said fragmentation route being assigned a prior probability appropriate to the chemical processes involved.

In preferred embodiments, apparatus according to the invention comprises a tandem mass spectrometer, and most preferably a tandem mass spectrometer that comprises a Time-of-Flight mass analyzer at least as its final stage. A Time-of-Flight mass analyzer is preferred because it is generally capable of greater mass measurement accuracy than a quadrupole analyzer. Preferably also the mass spectrometer comprises an electrospray ionization source into which an unknown peptide sample may be introduced.

BRIEF DESCRIPTION OF THE DRAWINGS

A preferred method of the invention will now be described in greater detail by reference to the figures, wherein:

FIG. 2 is a flow chart representing the operation of a method according to the invention.

DETAILED DESCRIPTION OF THE PREFERRED EMBODIMENT

Figure 1:
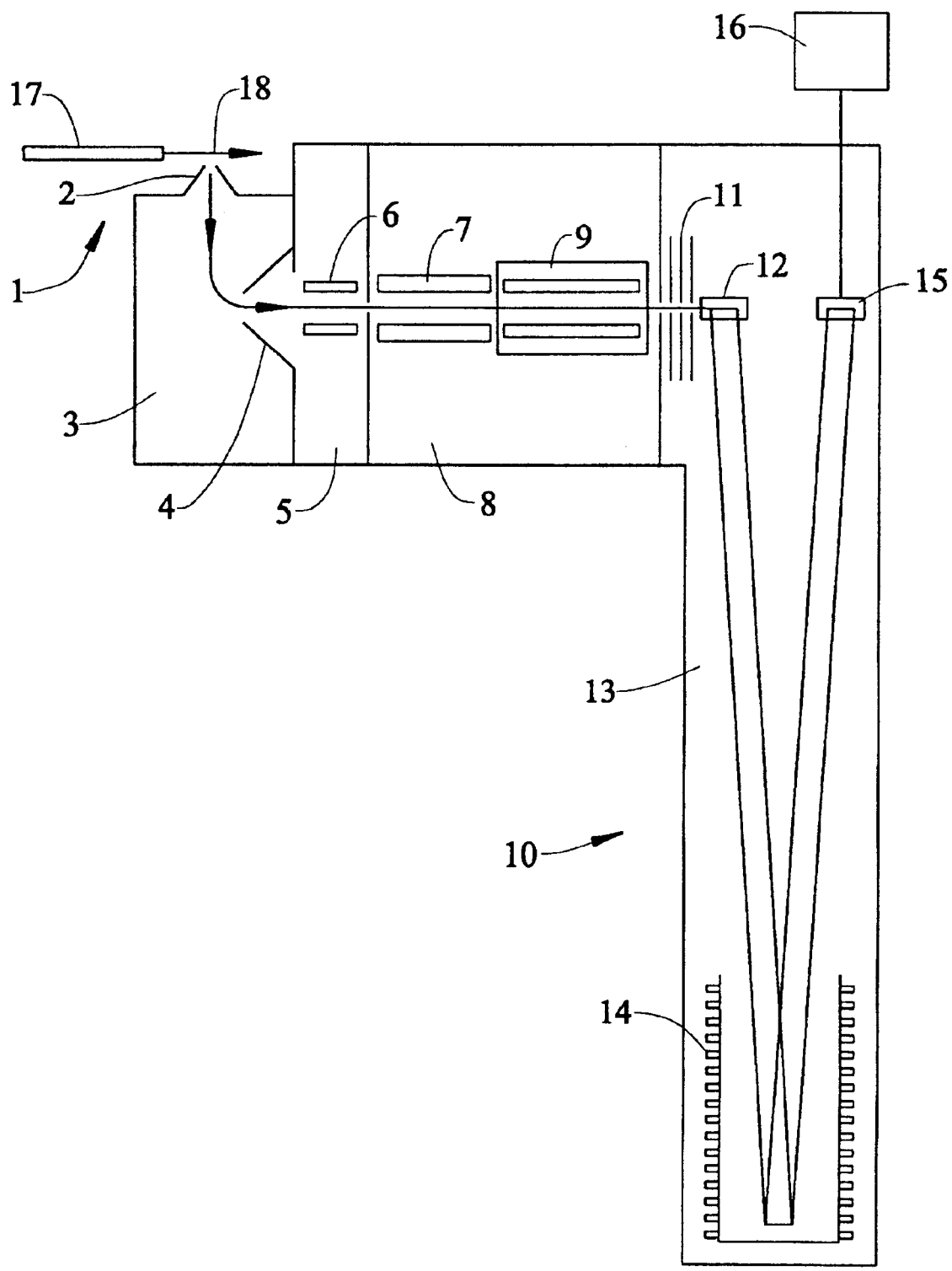
FIG. 1 is a schematic drawing of a tandem TOF mass spectrometer suitable for generating a mass spectrum from an unknown peptide sample.

Referring first to FIG. 1, the principal components of a tandem time-of-flight mass spectrometer suitable for carrying out methods according to the invention are shown in schematic form. An unknown peptide sample, or a mixture of such samples, is introduced into a capillary 17 comprised in an electrospray ion source generally indicated by 1. A jet 18 comprising ions characteristic of said peptide is generated in the source 1, and at least some of these ions pass through an aperture in a sampling cone 2 into a first evacuated chamber 3. From the chamber 3 the ions pass through an aperture in a skimmer cone 4 into a second evacuated chamber 5, and are then transported by means of a hexapole ion guide 6 into a quadrupole mass analyzer 7 disposed in a third evacuated chamber 8.

In a spectrometer of the kind illustrated in FIG. 1, the molecular weight of the peptide may be determined by using the mass analyzer 7 in a non mass-selective mode while a mass spectrum of the sample is acquired. Preferably, the molecular weight is determined to within ±0.5 daltons.

In order to record a fragmentation spectrum of an unknown peptide, the mass analyzer 7 may be set to transmit only the molecular ions of the unknown peptide (or a selected one of several peptides, if more than one is present in the sample). Molecular ions of the unknown peptide then pass from the mass analyzer 7 into a hexapole collision cell 9 which contains a collision gas (typically helium or argon) at a pressure between $10^{-3}$ and $10^{-2}$ torr and are fragmented to produce fragment ions which are indicative of the sequence of the unknown peptide. Typically, these fragment ions include ions formed by various losses of the amino acid residues from both the C and N termini of the peptide molecule, as discussed in more detail below.

The fragment ions formed in the collision cell 9 pass into a time-of-flight mass analyzer generally indicated by 10 via an electrostatic lens 11. In the time-of-flight analyzer 10, the ions are received by an ion-pusher 12 which causes bunches of ions to travel through a drift region 13 from the pusher to an ion-reflector 14, then back to an ion detector 15, as shown in FIG. 1. The mass of the ions is then determined by measuring the time taken for them to reach the detector 15 relative to the time they were ejected from the ion-pusher 12. A data acquisition system 16 controls this process and is programmed to carry out a method of the invention as discussed below. The mass range of the entire spectrometer should be at least 2500 daltons and it should preferably be capable of determining the masses of the fragment ions to at least ±0.5, and preferably ±0.05 daltons. A suitable mass spectrometer is obtainable from Micromass UK Ltd as the "Q-Tof".

Referring next to FIG. 2, a preferred method according to the invention begins by acquiring fragmentation mass spectrum of the unknown, peptide using the tandem mass spectrometer of FIG. 1.

The fragmentation spectrum is in practice complicated by the occurrence of multiply-charged ions and isotopic clusters (that is, several peaks associated with a single ion of a particular nominal mass consequent upon the natural abundance of different carbon, hydrogen, oxygen, nitrogen, and sulphur isotopes comprised in the ion). The method is therefore facilitated by conversion of the raw fragmentation spectrum to a "processable" spectrum. In such a spectrum, the multiply-charged ions may be converted to a corresponding singly charged ion at the appropriate nominal mass and the minor peaks comprised in each isotopic cluster are subsumed into the main peak representing the parent isotopic variant (i.e. that comprising $^{12}C$, $^{16}O$, $^{15}N$, $^{1}H$, $^{32}S$). The program "MaxEnt3™" available from Micromass UK Ltd. may be used for this purpose, but other software capable of these operations may be employed.

It is also preferable to represent each peak in the processable mass spectrum as a single nominal mass value together with an uncertainty value, for example 512.30±0.05 daltons, rather than as a series of real data points forming an approximately Gaussian peak as it would appear in the raw spectrum. The program "MaxEnt3™" also carries out this conversion, but any suitable peak recognition software could be employed. However, it has been found that the fidelity of the final most probable sequences predicted by methods according to the invention in strongly dependent on the range of the masses assigned to the constituent peaks in the processable mass spectrum. Consequently, both the calibration of the mass scale of the tandem mass spectrometer and the conversion of the raw peaks to their normal masses and their uncertainties must be carried out carefully and rigorously. It has been found that the intensities of the peaks in the fragmentation spectrum have little value in predicting the sequence of an unknown peptide. Instead of intensities, therefore, the peak recognition software should calculate a probability that each peak actually has been detected in the fragmentation spectrum, rather than being due to noise or an interfering background. The program "MaxEnt3™" is also capable of this operation.

Once a processable spectrum has been produced from the sample protein or peptide, trial sequences may be generated pseudo-randomly in the case of a de novo sequencing method (see, for example, copending patent application GB 9907810.7), filed Apr. 6, 1999) or randomly or pseudo randomly selected from a library or database of protein sequences. Typically, these randomly generated or selected sequences may be constrained by the molecular weight of the peptide when that has been determined. In the case of sequences comprised in a database, partial sequences having the requisite molecular weight may be extracted from longer sequences in the database. According to the invention, the likelihood of each trial sequence accounting for the processable spectrum is calculated using a fragmentation model which sums probabilistically over all the ways in which a trial sequence might fragment and give rise to peaks in the processable mass spectrum. This model should incorporate as much chemical knowledge concerning the fragmentation of peptides in the tandem mass spectrometer as is available at the time it is constructed. A preferred model incorporates the production of the following series of ions:

a) The b series, (ions representing the N-terminal amino acid residues and the loss of C-terminal amino acid residues);

b) The y" series, (ions representing the C-terminal amino acid residues and the loss of N-terminal amino acid residues);

c) The a series, (b ions which have lost CO); and d) z" series, (y" ions which have lost $NH_3$);

e) more general loss of $NH_3$ or $H_2O$.

The two main series of ions (y" and b) are represented in the preferred fragmentation model by Markov Chains, one for each series. In each chain, the probability that a particular ion is observed is dependent on the probability of its predecessor. For example, principally because of charge location, the observed y" ions in a fragmentation spectrum tend to form a coherent series starting with $y_1$ and usually continuing for some way with $y_2$, $y_3$ . . . , perhaps fading out for a time but likely appearing again towards $y_{n-1}$ and finally the full molecule. A Markov chain models this behaviour by setting up the probability (P) of y ions being present as a recurrence relation:

$$P(y_1)=p_1 P(y_r)=p_r P(y_{r-1}) +q_r(1-P(y_{r-1}))$$

for r=2,3,4, . . . ,n where $P(y_r)$ is the probability of $y_r$ being present and the probability of $y_r$ being absent is $1-P(y_r)$. The coefficients p and q are transition probabilities that determine how likely the series is to begin, to end, and to (re-)start. A similar Markov chain may be set up to represent the b ions.

This is illustrated in FIG. 2 (in which "~" represents "not present"). Here the y" series starts with $y_1"$, which has probability $p_1$ of being present and hence probability $1-p_1$ of not being present. Similarly the b series starts with $b_1$, which has its probability $p_1$ of being present. The numerical values of these and other probabilities depend on the chemistry involved: in fact $p_1$ for the b series can be set at or near zero, to incorporate the observation that the $b_1$ ion is usually absent. If the $y_1$ ion is present, it induces $y_2$ with probability $p_2$, and if not, $y_2$ is induced with probability $q_2$, as shown on the right-ward arrows in FIG. 2. The fact that presence of $y_2$ would usually follow from presence of $y_1$, and conversely, is coded by setting $p_2 > \frac{1}{2}$ and $q_2\frac{1}{2}$.

This correlated structure, known as a Markov chain, is continued from $y_2$ to $y_3$ and similarly up to $y_n$. Another such chain defines the b series. Note that all combinatoric patterns of presence or absence occur in the model, although the transition probabilities are usually assigned so as to favour correlated presences and absences. Transition probabilities can be set according to the charge affinity of the residues, allied to physical bond strengths. For example, a y series is likely to be present at and after a proline residue, so that $p_r$ and $q_r$ would be assigned higher values if the residue r were proline than if it were another residue.

The primary Markov chains are supplemented by introducing probabilities that the b series ions may also suffer loss of CO to form ions in the a series, and that y" series ions can lose $NH_3$ to form z" series ions and there may be more general loss of $NH_3$ or $H_2O$. Each possible process is assigned a probability which depends on the chemistry involved, for example, the probability of water loss increases with the number of hydroxyl groups on the fragments side chains and would be zero if there are no such hydroxyl groups that could be lost. The fragmentation model also allows for the formation of internal sequences starting at any residue, according to a probability appropriate for that particular residue. Internal sequences are often observed starting at proline residues, so that the probability of one starting at a proline residue is therefore set high. FIG. 2 also illustrates these extensions.

The formation of Immonium ions (which are equivalent to the loss of CO and H from a single residue) is also incorporated in the fragmentation model. Only certain residues can generate these ions, and for those that do, appropriate probabilities are set. For example, histidine residues generally result in the formation of an immonium ion at mass 110.072 daltons, and the probability of this process is therefore set close to 100%.

It will be appreciated that the more realistic is the fragmentation model the faster and more faithful will be the inference of the sequence of the unknown peptide. Consequently, as the understanding of the chemical processes involved in the formation of the fragmentation spectra of peptides advances, it is within the scope of the invention to adjust the fragmentation model accordingly.

The fragmentation model is explicitly probabilistic, meaning that it produces a probability distribution over all the ways that a trial sequence might fragment (based on the fragmentation model) rather than a list of possible masses in a predicted spectrum. Thus, the likelihood factor is computed as the sum over all these many fragmentation possibilities, so that the fragmentation pattern for a trial sequence is automatically and individually adapted to the data comprised in the processable spectrum. In terms of probability theory, the likelihood factor of the processable spectrum $D_2$ given a particular trial sequence S is $$P(D \text{ GIVEN } S) = \sum_f P(D \text{ GIVEN } f) \, P(f \text{ GIVEN } S)$$

where $$\sum_f$$

represents the sum over all the permitted fragmentation patterns f,

P(D GIVEN f) is the probability of the processable spectrum assuming the particular fragmentation pattern f, and P(f GIVEN S) is the probability of having fragmentation f from the trial sequence S. P(D GIVEN f) is evaluated as the product over all the fragment masses of the probabilities that the individual fragment masses are present in the processable mass spectrum. As explained, this sum can be computed in polynomial time rather than in a time proportional to the exponentially large number of fragmentation patterns themselves.

Further, methods according to the invention calculate not only a meaningful probability figure for any given trial sequence, but also the probability of the assignment of each peak in the processable spectrum to a given amino acid residue loss. This quantifies confidence in the identification of the peptide and indicates the regions in a sequence about which some doubt may exist if a single match of very high probability cannot be achieved.

What is claimed is:
1. A method of identifying a most probable amino acid sequence(s) which would account for a fragmentation mass spectrum of a protein or peptide, said method comprising the steps of:
   a) Producing the fragmentation mass spectrum (D) from said protein or peptide;
   b) Providing a plurality of amino trial acid sequences;
   c) For each of a plurality of fragmentation routes (f) which together represent the possible ways that a trial amino acid sequence (S) will fragment, calculating:
      i) the probability P(D given f) of the fragmentation mass spectrum (D), assuming a particular fragmentation route (f); and
      ii) the probability P(f given S) of having the fragmentation route (f) from each of said trial sequences (S);
   d) Calculating a likelihood factor P(D given S) that each trial sequence (S) is the true amino acid sequence of said peptide or protein by summing probabilistically over said plurality of fragmentation route, such that:

P(D given S)=$\Sigma_f$P(D given f).P(f given S)

e) Selecting one or more of said trial sequences (S) which have the highest likelihood factors calculated in step d) as being the most probable amino acid sequence(s) of said protein or peptide.
2. The method as claimed in claim 1 wherein said plurality of fragmentation routes represents all the possible ways that said trial sequence might fragment.
3. The method as claimed in claim 1 wherein a sum calculated in step d) is calculated in polynominal time.
4. The method as claimed in claim 3 wherein the sum calculated in step d) is calculated in a time proportional to the number of amino acid residues in each trial sequence.

5. The method as claimed in claim 1 wherein at least one of said fragmentation routes is described by using one or more Markov chains to represent a series of ions generated by successive losses of amino acid residues, wherein the probability of an ion in said series being observed is influenced by the probability of a preceding ion in the series being observed.

6. The method as claimed in claim 1 wherein in step e) each trial amino acid sequence (S) is assigned a prior probability, and the probability of the trial sequence accounting for the fragmentation spectrum is calculated according to Bayesian theory, such that:

Probability (trial sequence (S) and fragmentation spectrum)=Prior probability (trail sequence (S))×likelihood factor wherein the likelihood factor P(D given S) is calculated according to step d).

7. The method according to claim 6 wherein said prior probability of a trial amino acid sequence is calculated according to an average natural abundance of the amino acid residues comprised in said amino acid trail sequence.

8. The method according to claim 6 wherein said prior probability of a trial amino acid sequence is assigned a higher value when said amino acid sequence is present in a sequence library thought to encompass said protein or peptide.

9. The method according to claim 1 wherein the probability P(f given S) of having a fragmentation route f from a trial sequence S is at least in part determined by the proton affinities of amino acid residues in said trial sequence.

10. The method according to claim 1 wherein the probability P(f given S) of having a fragmentation route f from a trail sequence S is at least in part determined by the physical strengths of bonds linking amino acid residues in said trial sequence.

11. The method according to claim 5 wherein said plurality of fragmentation routes comprises at least b and y" series of ions, wherein said b series is defined as comprising ions representing an N-terminal amino acid residue of the trial sequence and a successive loss of amino acids from a C-terminal residue of the trial sequence, and the y" series is defined as comprising ions representing the C-terminal amino acid residue of the trial sequence and a successive loss of amino acid residues from the N-terminal residue of the trial sequence.

12. The method according to claim 11 wherein said plurality of fragmentation routes comprises the production of the a series of ions defined as ions of the b series which have lost CO.

13. The method according to claim 11 wherein said plurality of fragmentation routes comprises the production of a z" series of ions, wherein said z" series is defined as ions of the y" series which have lost $NH_3$.

14. The method according to claim 12 wherein said plurality of fragmentation routes comprises the production of a z" series of ions, wherein said z" series is defined as ions of the y" series which have lost $NH_3$.

15. The method according to claims 11 wherein said plurality of fragmentation routes includes ions from any of the series of ions which have lost $NH_3$ or $H_2O$.

16. The method according to claim 11 wherein said plurality of fragmentation routes comprises the production of immonium ions equivalent to the loss of CO and H from any of the amino acid residues in said trial sequence.

17. The method according to claim 11 wherein said plurality of fragmentation routes comprises the generation of sub-sequences of amino acids which begin and end at amino acid residues internal to said protein or peptide.

18. The method according to claim 1 wherein the trail sequences provided in step b) are obtained from one or more libraries or databases containing sequences or partial sequences of known peptides and proteins.

19. The method according to claim 5 wherein the trial sequences of step b) are obtained from one or more libraries or databases containing sequences or partial sequences of known peptides and proteins.

20. The method according to claim 11 wherein at least some of the trial sequences of step b) are generated without consideration of any information relating to said protein or peptide.

21. The method according to claim 5 wherein at least some of the trial sequences of step b) are generated randomly without reference to any information relating to said protein or peptide.

22. The method according to claim 18 wherein only trial sequences having molecular weights within a given range are selected from said one or more libraries or databases for use in step b).

23. The method according to claim 20 wherein only randomly generated trial sequences having molecular weights within a given range are used in step b).

24. The method according to claim 6 wherein said prior probability is at least in part determined by a genus or origin of said protein or peptide.

25. The method according to claim 1 wherein said fragmentation spectrum comprises an experimentally observed spectrum of said protein or peptide.

26. The method according to claim 1 wherein said fragmentation spectrum is obtained by converting multiply-charged ions and isotopic clusters present in an experimentally observed spectrum to single intensity values at mass-to-charge values corresponding to a singly-charged ion or, in the case of isotopic clusters, to the singly-charged ion of the lowest mass isotope present in the cluster.

27. The method according to claim 26 further comprising the step of calculating, for each peak in said fragmentation spectrum, an uncertainty value for its mass-to-charge ratio and the probability that a peak at that mass-to-charge ratio has actually been observed.

28. The method according to claim 27 wherein said uncertainty value is based on the standard deviation of a Gaussian peak representing the peak in the experimentally observed spectrum.

29. The method according to claim 27 wherein said probability that a peak has actually been observed is based on a signal-to-noise ratio of the peak in the experimentally observed spectrum.

* * * * *